(12) United States Patent
Wachendorff-Neumann et al.

(10) Patent No.: US 7,208,510 B2
(45) Date of Patent: Apr. 24, 2007

(54) FUNGICIDAL COMBINATIONS OF ACTIVE SUBSTANCES

(75) Inventors: Ulrike Wachendorff-Neumann, Neuwied (DE); Herbert Gayer, Monheim (DE); Ulrich Heinemann, Leichlingen (DE); Thomas Seitz, Langenfeld (DE); Bernd-Wieland Krüger, Bergisch Gladbach (DE); Wolfgang Krämer, Burscheid (DE); Lutz Aβmann, Langenfeld (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 11/336,501

(22) Filed: Jan. 20, 2006

(65) Prior Publication Data

US 2006/0172981 A1 Aug. 3, 2006

Related U.S. Application Data

(62) Division of application No. 10/619,730, filed on Jul. 15, 2003, which is a division of application No. 10/149,353, filed as application No. PCT/EP00/11989 on Nov. 30, 2000, now Pat. No. 6,624,183.

(30) Foreign Application Priority Data

Dec. 13, 1999 (DE) .............................. 199 59 947
May 3, 2000 (DE) .............................. 100 21 412

(51) Int. Cl.
*A10N 43/78* (2006.01)
(52) U.S. Cl. ............................ 514/367
(58) Field of Classification Search ............... 514/367
See application file for complete search history.

(56) References Cited

U.S. PATENT DOCUMENTS

| | | | |
|---|---|---|---|
| 1,972,961 A | 9/1934 | Tisdale et al. ........... 167/22 |
| 2,553,770 A | 5/1951 | Kittleson ................ 167/33 |
| 3,290,353 A | 12/1966 | Battershell et al. ..... 260/465 |
| 3,513,241 A | 5/1970 | Hoyer et al. ........... 424/300 |
| 3,745,170 A | 7/1973 | Fujinami et al. ........ 260/326.5 |
| 3,755,350 A | 8/1973 | Sauli ..................... 260/309.5 |
| 3,823,240 A | 7/1974 | Sauli ..................... 424/273 |
| 3,903,090 A | 9/1975 | Fujinami et al. ........ 260/281 |
| 3,912,752 A | 10/1975 | Meiser et al. .......... 260/308 R |
| 3,952,002 A | 4/1976 | Kramer et al. ......... 260/308 R |
| 3,991,071 A | 11/1976 | Brookes et al. ........ 260/309 |
| 4,009,278 A | 2/1977 | Fujinami et al. ....... 424/274 |
| 4,048,318 A | 9/1977 | Meiser et al. .......... 424/269 |
| 4,079,062 A | 3/1978 | Van Reet et al. ...... 260/308 |
| 4,147,791 A | 4/1979 | Meiser et al. .......... 424/269 |
| 4,154,945 A | 5/1979 | Brookes et al. ........ 548/341 |
| 4,160,838 A | 7/1979 | Van Reet et al. ...... 424/269 |
| 4,291,049 A | 9/1981 | Bosone et al. ......... 424/275 |
| 4,331,670 A | 5/1982 | Nishiyama et al. ..... 424/263 |
| 4,347,253 A | 8/1982 | Harr ....................... 424/272 |
| 4,425,357 A | 1/1984 | Bosone et al. ......... 424/278 |
| 4,432,989 A | 2/1984 | Spencer ................. 424/273 R |
| 4,436,744 A | 3/1984 | Harr ....................... 424/272 |
| 4,457,937 A | 7/1984 | Sandmeier et al. .... 424/272 |
| 4,496,551 A | 1/1985 | Moberg .................. 514/63 |
| 4,510,136 A | 4/1985 | Moberg .................. 514/63 |
| 4,532,341 A | 7/1985 | Holmwood et al. .... 549/559 |
| 4,608,385 A | 8/1986 | Noguchi et al. ........ 514/444 |
| 4,626,595 A | 12/1986 | Holmwood et al. .... 549/559 |
| 4,664,696 A | 5/1987 | Schaub .................. 71/92 |
| 4,723,984 A | 2/1988 | Holmwood et al. .... 71/76 |
| 4,780,551 A | 10/1988 | Nyfeler et al. ......... 549/422 |
| 4,789,672 A | 12/1988 | Holmwood et al. .... 514/184 |
| 4,849,439 A | 7/1989 | Schaub .................. 514/383 |
| 4,851,405 A | 7/1989 | Kramer et al. ......... 514/212 |
| 4,871,390 A | 10/1989 | Holmwood et al. .... 71/92 |
| 4,897,107 A | 1/1990 | Holmwood et al. .... 71/92 |
| 4,904,298 A | 2/1990 | Holmwood et al. .... 71/92 |
| 4,910,200 A | 3/1990 | Curtze et al. ........... 514/237 |
| 4,911,746 A | 3/1990 | Holmwood et al. .... 71/92 |
| 4,920,139 A | 4/1990 | Fujimoto ............... 514/383 |
| 4,925,840 A | 5/1990 | Nyfeler et al. ......... 514/228 |
| 4,931,560 A | 6/1990 | Hubele .................. 544/315 |
| 4,931,581 A | 6/1990 | Schurter et al. ........ 560/18 |
| 4,957,933 A | 9/1990 | Geffken et al. ........ 514/376 |
| 4,988,734 A | 1/1991 | Kraatz et al. .......... 514/624 |

(Continued)

FOREIGN PATENT DOCUMENTS

| | | |
|---|---|---|
| DE | 2012656 | 9/1971 |
| DE | 610764 | 8/1994 |
| DE | 775696 | 5/1997 |
| WO | 98/23155 | 6/1998 |

OTHER PUBLICATIONS

Pesticide Manual, 9th Ed. (month unavailable) 1991, pp. 206, 249, 431, 443, 461, 491, 529, 531, 554, 654, 726, 827.

*Primary Examiner*—Alton Pryor
(74) *Attorney, Agent, or Firm*—Richard E. L. Henderson

(57) ABSTRACT

The present invention relates to fungicidally active compound combinations of a fluorobenzothiazole derivative of the formula (I)

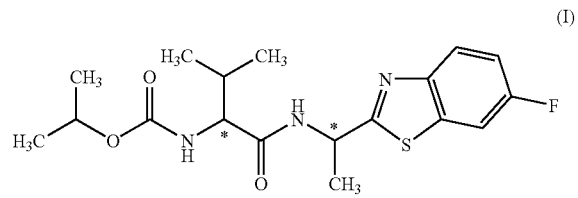

and at least one of the compounds listed in the disclosure.

2 Claims, No Drawings

U.S. PATENT DOCUMENTS

| | | | |
|---|---|---|---|
| 4,992,438 A | 2/1991 | Ito et al. | 514/275 |
| 4,995,898 A | 2/1991 | Nasu et al. | 71/90 |
| 4,997,941 A | 3/1991 | Hubele | 544/332 |
| 5,021,581 A | 6/1991 | Clough et al. | 546/309 |
| 5,059,623 A | 10/1991 | Kruger et al. | 514/613 |
| 5,081,141 A | 1/1992 | Colle et al. | 514/383 |
| 5,087,635 A | 2/1992 | Shaber | 514/383 |
| 5,145,843 A | 9/1992 | Arnold et al. | 514/63 |
| 5,145,856 A | 9/1992 | Clough et al. | 514/274 |
| 5,153,200 A | 10/1992 | Hubele | 514/275 |
| 5,190,928 A | 3/1993 | Schurter et al. | 514/63 |
| 5,221,691 A | 6/1993 | Clough et al. | 514/619 |
| 5,223,523 A | 6/1993 | Adams, Jr. et al. | 514/376 |
| 5,240,940 A | 8/1993 | Arnold et al. | 514/312 |
| 5,264,440 A | 11/1993 | Clough et al. | 514/269 |
| 5,266,585 A | 11/1993 | Hubele et al. | 514/383 |
| 5,304,572 A | 4/1994 | Michelotti et al. | 514/514 |
| 5,334,607 A | 8/1994 | Sauter et al. | 514/378 |
| 5,340,802 A | 8/1994 | Shiosaki et al. | 514/18 |
| 5,342,837 A | 8/1994 | Clough et al. | 514/247 |
| 5,356,908 A | 10/1994 | Geffken et al. | 514/333 |
| 5,389,308 A | 2/1995 | Busel et al. | 252/587 |
| 5,395,837 A | 3/1995 | Clough et al. | 514/269 |
| 5,407,902 A | 4/1995 | Oda et al. | 504/336 |
| 5,438,059 A | 8/1995 | Clough et al. | 514/256 |
| 5,453,531 A | 9/1995 | Seitz et al. | 560/29 |
| 5,468,747 A | 11/1995 | Clough et al. | 514/239.5 |
| 5,523,311 A | 6/1996 | Schurter et al. | 548/361 |
| 5,679,676 A | 10/1997 | Kruger et al. | 514/229.2 |
| 5,789,428 A * | 8/1998 | Shibata et al. | 514/367 |
| 5,789,430 A | 8/1998 | Jautelat et al. | 514/272.4 |
| 5,859,039 A | 1/1999 | Jautelat et al. | 514/384 |
| 5,883,250 A | 3/1999 | Kruger et al. | 540/544 |
| 6,020,338 A * | 2/2000 | Pfrengle et al. | 514/259.31 |
| 6,020,354 A | 2/2000 | Assmann et al. | 514/380 |
| 6,103,717 A | 8/2000 | Heinemann et al. | 514/229.2 |
| 6,127,547 A | 10/2000 | Assmann et al. | 548/302.1 |
| 6,130,251 A | 10/2000 | Seitz et al. | 514/620 |
| 6,160,001 A | 12/2000 | Assmann et al. | 514/395 |
| 6,235,743 B1 | 5/2001 | Gayer et al. | 514/269 |
| 6,268,508 B1 | 7/2001 | Assmann et al. | 548/302.1 |
| 6,355,634 B1 | 3/2002 | Isenring et al. | 514/227.5 |
| 6,359,133 B2 | 3/2002 | Gayer et al. | 544/318 |
| 6,387,939 B1 | 5/2002 | Assmann et al. | 514/395 |
| 6,624,183 B2 * | 9/2003 | Wachendorff-Neumann et al. | 514/367 |
| 2001/0018442 A1 | 8/2001 | Gayer et al. | 514/269 |

\* cited by examiner

FUNGICIDAL COMBINATIONS OF ACTIVE SUBSTANCES

RELATED APPLICATIONS

This application is a division of U.S. application Ser. No. 10/619,730, filed Jul. 15, 2003, which is a division of U.S. application Ser. No. 10/149,353, filed Jun. 7, 2002, now U.S. Pat. No. 6,624,183, issued Sep. 23, 2003, which was filed under 35 U.S.C. 371 as a national stage application of International Application No. PCT/EP00/11989, filed Nov. 30, 2000, which was published in German as International Patent Publication WO 01/44215 on Jun. 21, 2001, which is entitled to the right of priority of German Patent Applications 199 59 947.5, filed Dec. 13, 1999, and 100 21 412.6, filed May 3, 2000.

The present invention relates to novel active compound combinations which consist of a known fluoro-benzothiazole derivative and further known fungicidally active compounds, and which are highly suitable for controlling phytopathogenic fungi.

It is already known that isopropyl 1-({[1-(6-fluoro-1,3-benzothiazol-2-yl)ethyl]-amino}carbonyl)-2-methylpropyl-carbamate has fungicidal properties (cf. EP-A1-775 696). The activity of this compound is good; however, at low application rates it is in some cases not satisfactory.

Furthermore, it is already known that a large number of triazole derivatives, aniline derivatives, dicarboximides and other heterocycles can be employed for controlling fungi (cf. EP-A 0 040 345, DE-A 22 01 063, DE-A 23 24 010, Pesticide Manual, 9th Edition (1991), pages 249 and 827, EP-A 0 382 375 and EP-A 0 515 901). Likewise, the activity of these compounds is not always satisfactory at low application rates.

Finally, it is also known that 1-[(6-chloro-3-pyridinyl)-methyl]-N-nitro-2-imidazolidineimine can be used for controlling animal pests such as insects (cf. Pesticide Manual, 9th Edition (1991), page 491). However, fungicidal properties have hitherto not been described for this compound.

Furthermore, it is already known that 1-(3,5-dimethyl-isoxazol-4-sulphonyl)-2-chloro-6,6-difluoro-[1,3]-dioxolo-[4,5f]-benzimidazole has fungicidal properties (cf. WO 97-06171).

Furthermore, it is already known that substituted azodioxacycloalkenes have fungicidal properties (cf. EP-B-712 396).

Finally, it is also known that substituted halogenopyrimidines have fungicidal properties (cf. DE-A1-196 46 407, EP-B-712 396).

It has now been found that the novel active compound combinations comprising a fluorobenzothiazole derivative of the formula

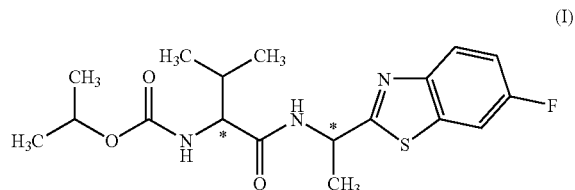

(I)

and (1) a triazole derivative of the formula

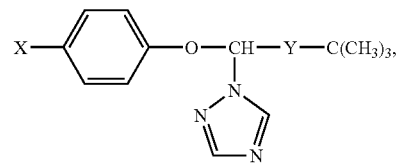

(II)

in which
X represents chlorine or phenyl and
Y represents

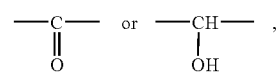

and/or
(2) the triazole derivative of the formula

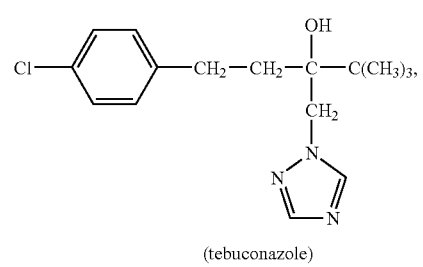

(III)

(tebuconazole)

and/or
(3) an aniline derivative of the formula

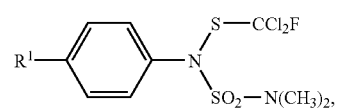

(IV)

in which
R¹ represents hydrogen or methyl,
and/or
(4) N-[1-(4-chloro-phenyl)-ethyl]-2,2-dichloro-1-ethyl-3-methyl-cyclopropane-carboxamide of the formula

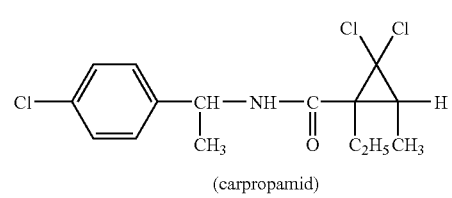

(V)

(carpropamid)

and/or
(5) the zinc propylene-1,2-bis-(dithiocarbamidate) of the formula

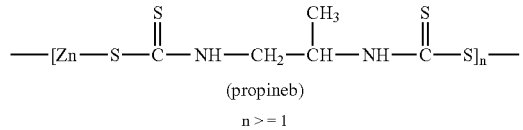

(propineb)

n >= 1 and/or
(6) at least one thiocarbamate of the formula

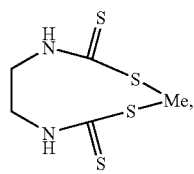

Me=Zn or Mn or a mixture of Zn and Mn and/or
(7) the aniline derivative of the formula

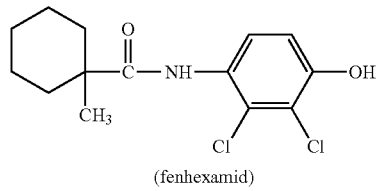

(fenhexamid)

and/or
(8) the compound of the formula

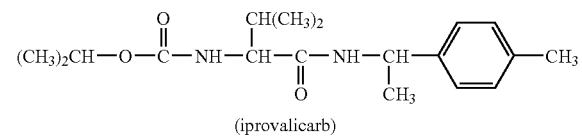

(iprovalicarb)

and/or
(9) the benzothiadiazole derivative of the formula

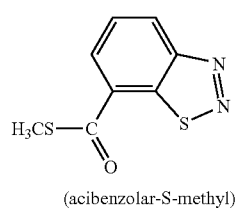

(acibenzolar-S-methyl)

and/or
(10) the 8-t-butyl-2-(N-ethyl-N-n-propyl-amino)-methyl-1,4-dioxaspiro[5,4]-decane of the formula

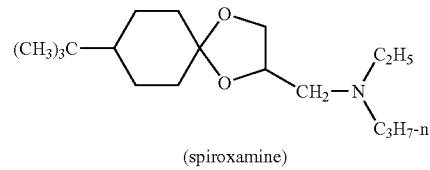

(spiroxamine)

and/or
(11) the compound of the formula

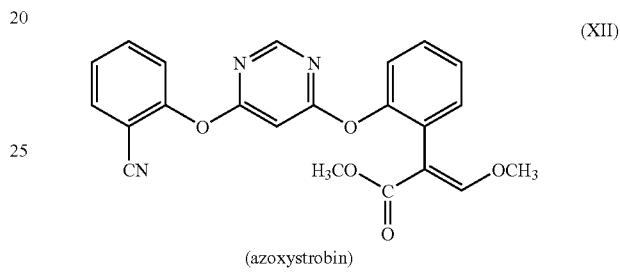

(azoxystrobin)

and/or
(12) the compound of the formula

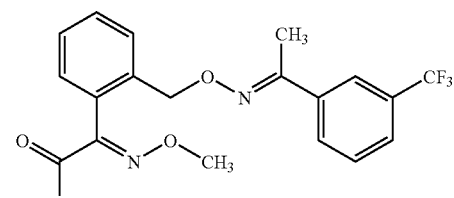

(trifloxystrobin)

and/or
(13) the compound of the formula

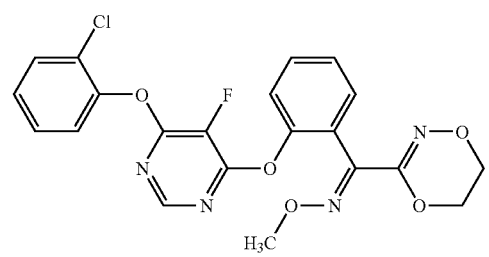

and/or
(14) the cyanoxime derivative of the formula

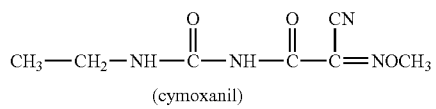
(XV)

(cymoxanil)

and/or
(15) a pyrimidine derivative of the formula

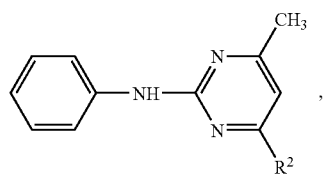
(XVI)

in which
R² represents methyl, —C≡C—CH₃ (mepanipyrim) or cyclopropyl (cyprodinyl), and/or
(16) an aniline derivative of the formula

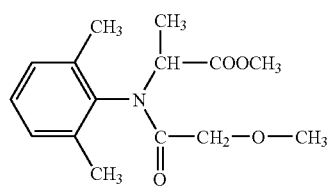
(XVII)

(metalaxyl or metalaxyl M)

and/or
(17) the morpholine derivative of the formula

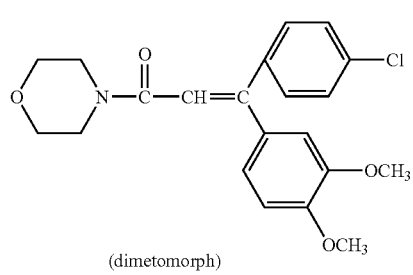
(XVIII)

(dimetomorph)

and/or
(18) the phthalimide derivative of the formula

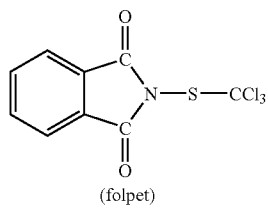
(XIX)

(folpet)

and/or
(19) the phosphorus compound of the formula

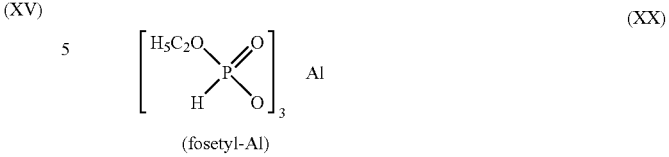
(XX)

(fosetyl-Al)

and/or
(20) the hydroxyethyl-triazole derivative of the formula

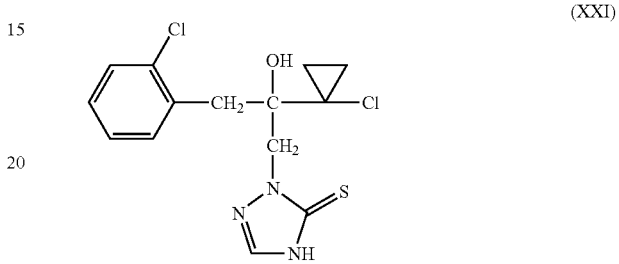
(XXI)

and/or
(21) the 1-[(6-chloro-3-pyridinyl)-methyl]-N-nitro-2-imidazolidinimine of the formula

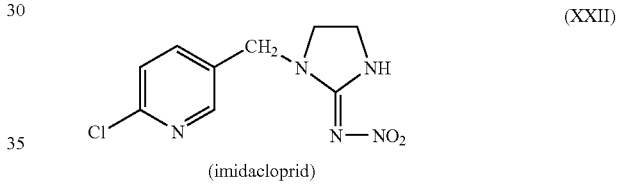
(XXII)

(imidacloprid)

and/or
(22) the oxazolidinedione of the formula

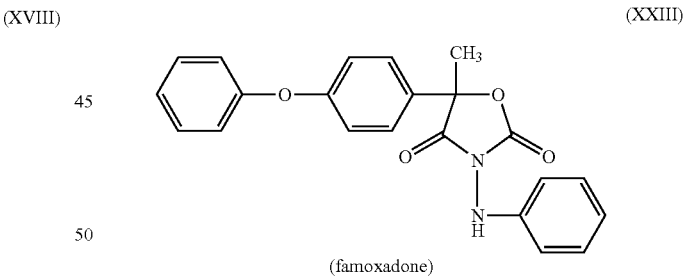
(XXIII)

(famoxadone)

and/or
(23) the benzamide derivative of the formula

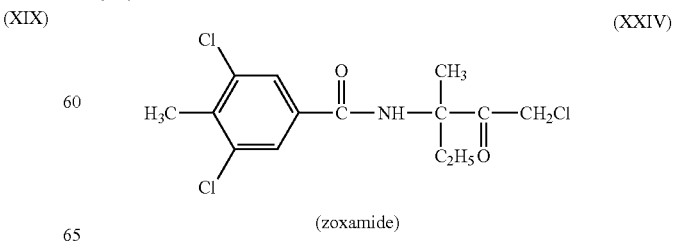
(XXIV)

(zoxamide)

and/or
(24) a guanidine derivative of the formula $$R^3-\underset{H}{N}-(CH_2)_8-[\underset{|}{\overset{R^3}{N}}-(CH_2)_8]_m-\underset{|}{\overset{R^3}{N}}-H$$

x (2 + m) CH₃COOH (XXV)

in which m represents integers from 0 to 5 and

R³ represents hydrogen (17 to 23%) or the radical of the formula $$-\underset{NH_2}{\overset{}{C}}=NH$$

(77 to 83%)

and/or
(25) the triazole derivative of the formula (XXVI)

(penconazole)

and/or
(26) the halogeno-benzimidazole of the formula (XXVII)

and/or
(27) the halogenopyrimidine of the formula (XXVIII)

and/or
(28) the tetrachloro-isophthalo-dinitrile of the formula (XXIX)

(chlorothalonil)

and/or
(29) the compound of the formula (XXX)

(propamocarb)

and/or
(30) the pyridineamine of the formula (XXXI)

(fluazinam)

and/or
(31) the thiazolecarboxamide of the formula (XXXII)

(ethaboxam)

and/or
(32) the sulphonamide of the formula (XXXIII)

(cyamidazosulfamid)

and/or
(33) the compound of the formula (XXXIV)

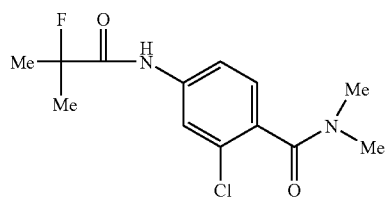

and/or
(34) the compound of the formula (XXXV)

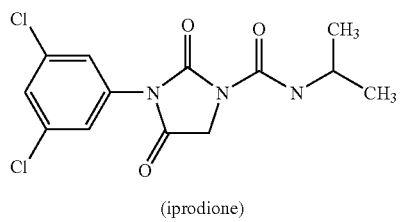

(iprodione)

and/or
(35) the compound of the formula (XXXVI)

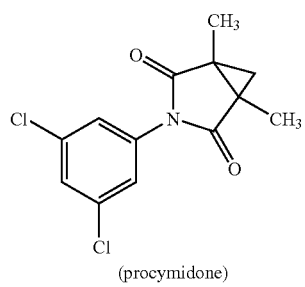

(procymidone)

and/or
(36) the diamide of the formula (XXXVII)

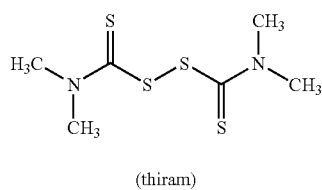

(thiram)

and/or
(37) the methoxyacrylate derivative of the formula (XXXVIII)

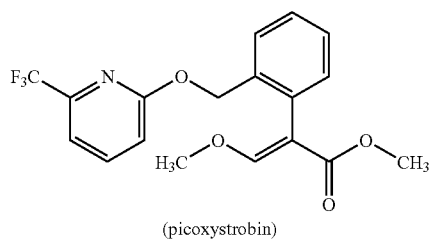

(picoxystrobin)

and/or
(38) the quinoline derivative of the formula (XXXIX)

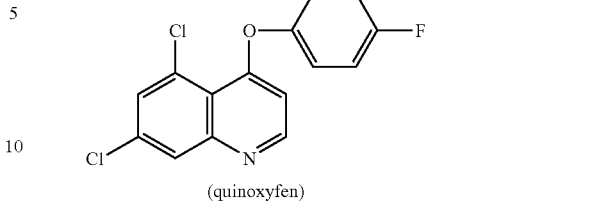

(quinoxyfen)

and/or
(39) the phenylamide derivative of the formula (XXXX)

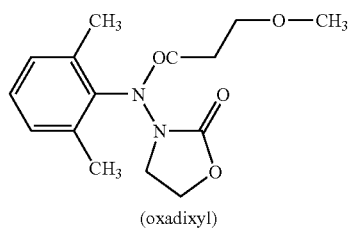

(oxadixyl)

and/or
(40) the phenylamide derivative of the formula (XXXXI)

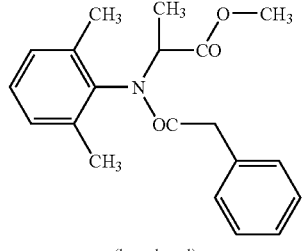

(benalaxyl)

and/or
(41) the dicarboxime derivative of the formula (XXXXIIa)

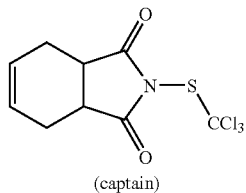

(captain)

and/or
(42) the phosphonic acid of the formula (XXXXIII)

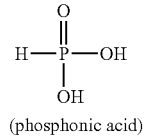

(phosphonic acid)

and/or
(43) the pyrrole derivative of the formula

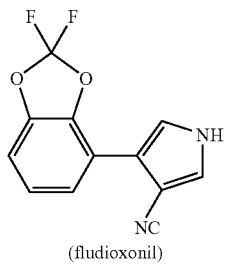
(fludioxonil)

and/or
(44) the phenyl carbonate of the formula

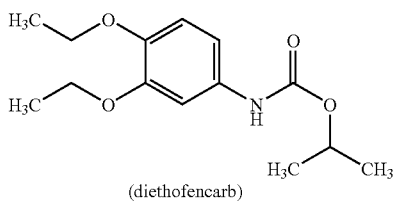
(diethofencarb)

and/or
(45) the copper compounds
a) copper oxychloride (XXXXVIa)
b) copper hydroxid (XXXXVIb)
and/or
(46) the imidazole derivative of the formula (XXXXVII)

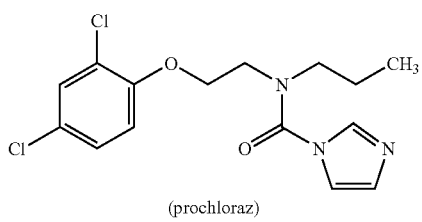
(prochloraz)

and/or
(47) the triazole derivative of the formula
a)

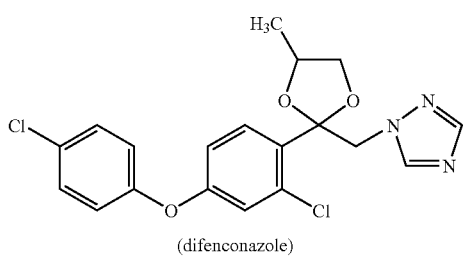
(difenconazole)

and/or
b)

(XXXXVIIIb)

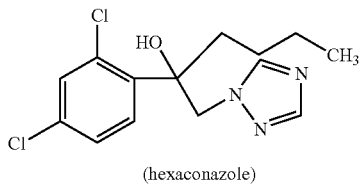
(hexaconazole)

and/or
c)

(XXXXVIIIc)

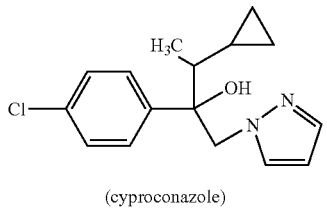
(cyproconazole)

and/or
d)

(XXXXVIIId)

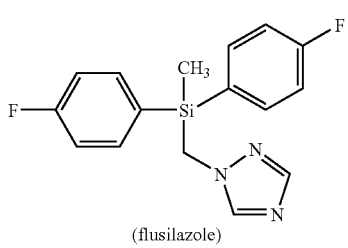
(flusilazole)

and/or
e)

(XXXXVIIIe)

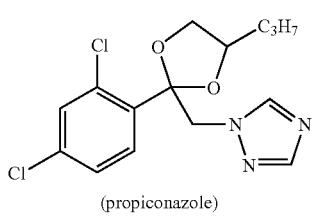
(propiconazole)

and/or
f)

(XXXXVIIIf)

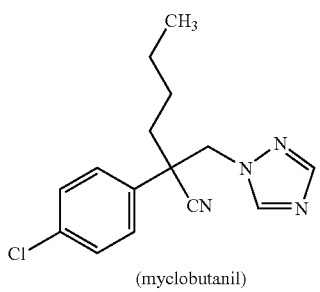
(myclobutanil)

and/or
g)

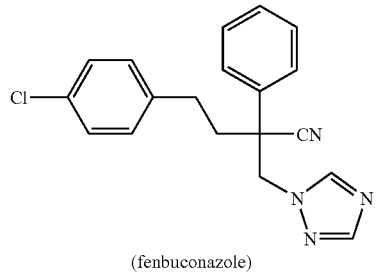

(XXXXVIIIg)

(fenbuconazole)

and/or
h)

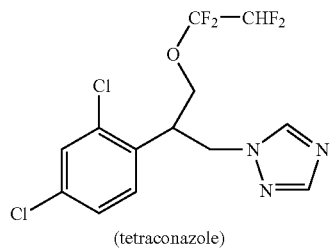

(XXXXVIIIh)

(tetraconazole)

and/or
(48) a compound of the general formula

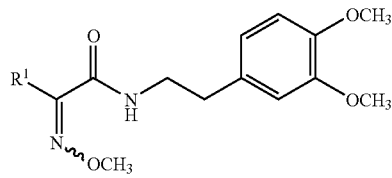

(XXXXIX)

in which
R¹ represents unsubstituted or fluorine-, chlorine-, bromine-, methyl- or ethyl-substituted phenyl, 2-naphthyl, 1,2,3,4-tetrahydronaphthyl or indanyl, and/or
(49) N-methyl-2-(methoxyimino)-2-[2-([1-(3-tri-fluoro-methyl-phenyl)ethoxy]iminomethyl)phenyl]acetamide of the formula

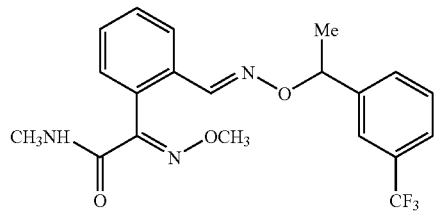

(XXXXX)

and/or
(50) 2,4-dihydro-5-methoxy-2-methyl-4-[2-([([1-(3-tri-fluoro-methylphenyl)ethylidene]amino)oxy]methyl)phenyl]-3H-1,2,4-triazol-3-one of the formula

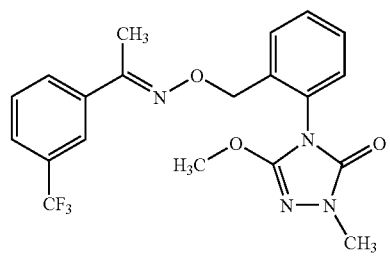

(XXXXXI)

and/or
(51) the compound of the formula (XXXXXII)

$F_3C$ ... Me ... N–O ... Me–NH ... N–O–Me have very good fungicidal properties.

Surprisingly, the fungicidal activity of the active compound combinations according to the invention is considerably higher than the sum of the activities of the individual active compounds. Thus, an unforeseeable, true synergistic effect is present, and not just an addition of activities.

From the structural formula of the active compound of the formula (I), it can be seen that the compound has two asymmetrically substituted carbon atoms. Accordingly, the product can be present as a mixture of different isomers or else in the form of a single isomer.

Preferred compounds of the formula (I) are compounds in which the amino acid moiety is formed from i-propyloxycarbonyl-L-valine and the fluoro-benzothiazoleethylamine moiety is racemic, but has, in particular, the (R) configuration.

The formula (II) includes the compounds
1-(4-chloro-phenoxy)-3,3-dimethyl-1-(1,2,4-triazol-1-yl)-butan-2-one of the formula

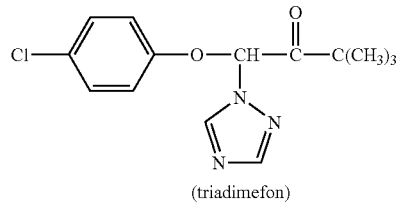

(IIa)

(triadimefon)

1-(4-chloro-phenoxy)-3,3-dimethyl-1-(1,2,4-triazol-1-yl)-butan-2-ol of the formula (IIb)
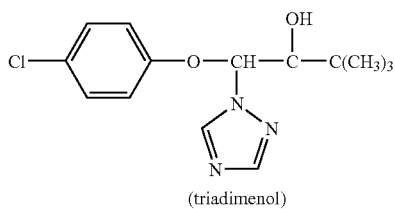
(triadimenol)

and
1-(4-phenyl-phenoxy)-3,3-dimethyl-1-(1,2,4-triazol-1-yl)-butan-2-ol of the formula (IIc)
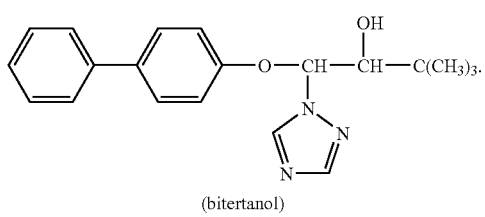
(bitertanol)

The formula (IV) includes the aniline derivatives of the formulae (IVa)
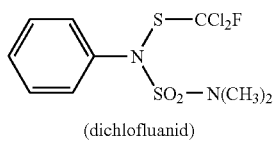
(dichlofluanid)

and (IVb)
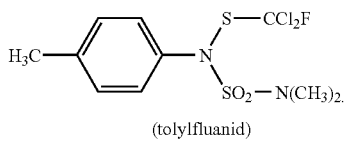
(tolylfluanid)

It is evident from the structural formula for the active compound of the formula (V) that the compound has three asymmetrically substituted carbon atoms. The product may therefore be present as a mixture of different isomers, or else in the form of a single component. Particular preference is given to the compounds N-(R)-[1-(4-chloro-phenyl)-ethyl]-(1S)-2,2-dichloro-1-ethyl-3t-methyl-1R-cyclopropanecarboxamide of the formula (Va)
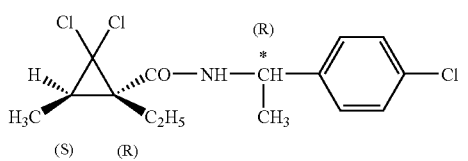

and
N-(R)-[1-(4-chloro-phenyl)-ethyl]-(1R)-2,2-dichloro-1-ethyl-3t-methyl-1R-cyclopropanecarboxamide of the formula (Vb)
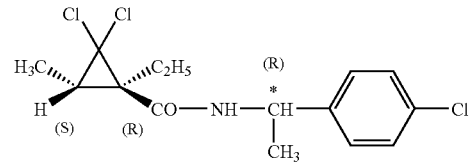

The formula (VII) includes the compounds (VIIa) Me=Zn (zineb), (VIIb) Me=Mn (maneb) and (VIIc) mixture of (VIIa) and (VIIb) (mancozeb).

The formula (XVI) includes the compounds (XVIa)
$R^2 = CH_3$
(pyrimethanil) and (XVIb)
$R^2 =$ 
(cyprodinyl)

(XVIc)
$R^2 = —C≡C—CH_3$
(mepanipyrim)

The compound of the formula (XVII) can be present as methyl N-(2,6-dimethylphenyl)-N-(methoxyacetyl)-DL-alaninate (metalaxyl, XVIIa) or as methyl N-(2,6-dimethylphenyl)-N-(methoxyacetyl)-D-alaninate (metalaxyl-M, XVIIb).

The hydroxyethyl-triazole derivative of the formula (XXI) can be present in the "thiono" form of the formula (XXI)
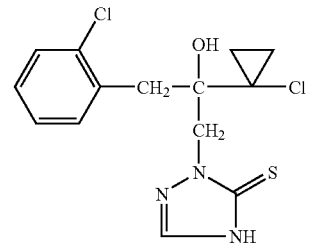

or in the tautomeric "mercapto" form of the formula (XXIb)
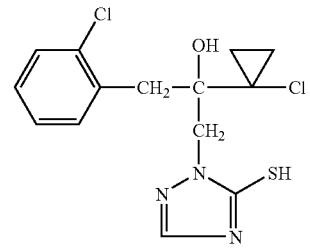

For simplicity's sake, only the "thiono" form is given in each case.

The guanidine derivative of the formula (XXV) is a substance mixture with the common name guazatine.

From the structural formula for the active compounds of the formula (XXXXIX), it can be seen that the compounds can be present as E or Z isomers. Accordingly, the product can be present as a mixture of different isomers or else in the form of a single isomer. Preference is given to compounds of the formula (XXXXIX) in which the compounds of the formula (XXXXIX) are present as E isomer. Particular preference is given to the compounds of the formulae

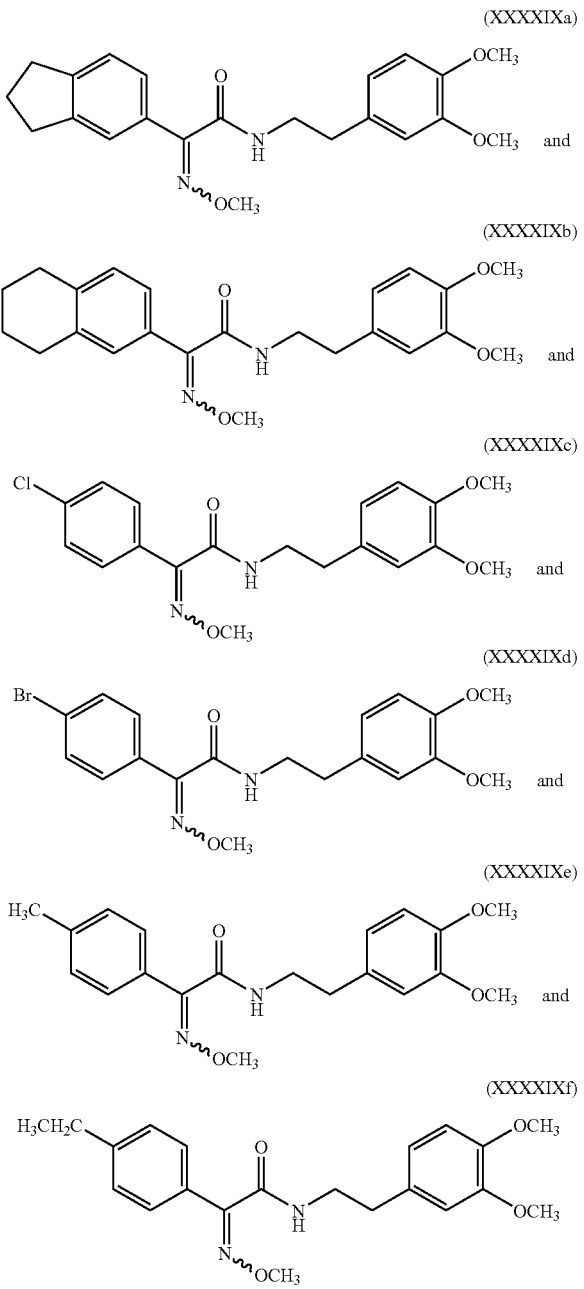

and their isomers.

The following active compounds are particularly preferred mixing partners of the compounds of the formula (I):
(3) tolylfluanid (IVb),
(5) propineb (VI),
(6) mancozeb (VIIc),
(7) fenhexamid (VIII),
(8) iprovalicarb (VIII),
(11) azoxystrobin (XII),
(12) trifloxystrobin (XIII),
(13) compound of the formula (XIV),
(18) folpet (XIX),
(20) compound of the formula (XXI),
(26) compound of the formula (XXVII),
(27) compound of the formula (XXVIII),
(28) chlorothalonil (XXIX),
(30) fluazinam (XXXI), and
(45) copper compounds
  a) copper oxychloride (XXXXVIa)
  b) copper hydroxide (XXXXVIb).

The components which are present in the active combinations according to the invention in addition to a halogenobenzimidazole of the formula (XXVII) are also known.

Specifically, the active compounds are described in the following publications:
(1) compounds of the formula (II)
  DE-A 22 01 063
  DE-A 23 24 010
(2) compound of the formula (III)
  EP-A 0 040 345
(3) compounds of the formula (IV)
  Pesticide Manual, 9th Ed. (1991), pages 249 and 827
(4) compound of the formula (V) and individual derivatives thereof.
  EP-A 0 341 475
(5) compound of the formula (VI)
  Pesticide Manual, 9th Ed. (1991), page 726
(6) compounds of the formula (VII)
  Pesticide Manual, 9th Ed. (1991), pages 529, 531 and 866
(7) compound of the formula (VIII)
  EP-A 0 339 418
(8) compound of the formula (IX)
  EP-A 0 472 996
(9) compound of the formula (X)
  EP-A 0 313 512
(10) compound of the formula (XI)
  EP-A 0 281 842
(11) compound of the formula (XII)
  EP-A 0 382 375
(12) compound of the formula (XIII)
  EP-A460 575
(13) compound of the formula (XIV)
  DE-A 196 02 095
(14) compound of the formula (XV)
  Pesticide Manual, 9th Ed. (1991), page 206
(15) compounds of the formula (XVI)
  EP-A 0 270 111
  EP-A 0 310 550
(16) compound of the formula (XVII)
  Pesticide Manual, 9th Ed. (1991), page 554
(17) compound of the formula (XVIII)
  EP-A0219 756
(18) compound of the formula (XIX)
  Pesticide Manual, 9th Ed. (1991), page 431
(19) compound of the formula (XX)
  Pesticide Manual, 9th Ed. (1991), page 443
(20) compound of the formula (XXI)
  WO 96-16048
(21) compound of the formula (XXII)
  Pesticide Manual, 9th Ed. (1991), page 491
(22) compound of the formula (XXII)
  EP-A 0 393 911
(23) compound of the formula (XXIV)
  EP-A 0 600 629
(24) substance of the formula (XXV)
  Pesticide Manual, 9th Ed. (1991), page 461
(25) compound of the formula (XXVI)
  Pesticide Manual, 9th Ed. (1991), page 654

(26) compound of the formula (XXVII)
WO 97-06171
(27) compound of the formula (XXVIII)
DE-A1-196 46 407, EP-B-0 712 396
(28) compound of the formula (XXIX)
U.S. Pat. No. 3,290,353
(29) compound of the formula (XXX)
DE-A-156 7169
(30) compound of the formula (XXXI)
EP-A-0 031 257
(31) compound of the formula (XXXII)
EP-A-0 639 547
(32) compound of the formula (XXXI)
EP-A-0 298 196
(33) compound of the formula (XXXIV)
EP-A-600 629
(34) compound of the formula (XXXV)
DE-A-2 149 923
(35) compound of the formula (XXXVI)
DE-A-2 012 656
(36) compound of the formula (XXXVII)
U.S. Pat. No. 1,972,961
(37) compound of the formula (XXXVIII)
EP-A-326 330
(38) compound of the formula (XXXI)
EP-A 278 595
(39) compound of the formula (XXXX)
DE-A-3 030 026
(40) compound of the formula (XXXXI)
DE-A-2 903 612
(41) compound of the formula (XXXXII)
U.S. Pat. No. 2,553,770
(42) compound of the formula (XXXXIII)
known and commercially available
(43) compound of the formula (XXXXIV)
EP-A-206 999
(44) compound of the formula (XXXXV)
EP-A-78 663
(45) a) compound of the formula (XXXXVIa)
known and commercially available
b) compound of the formula (XXXXVIb)
known and commercially available
(46) compound of the formula (XXXXVII)
DE-A-2 429 523
(47) a) compound of the formula (XXXXVIa)
EP-A-112 284
b) compound of the formula (XXXXVIIIb)
DE-A-3 042 303
c) compound of the formula (XXXXVIIIc)
DE-A-3 406 993
d) compound of the formula (XXXXVIIId)
EP-A-68 813
e) compound of the formula (XXXXVIIIe)
DE-A-2551560
f) compound of the formula (XXXXVIIIf)
EP-A-145 294
g) compound of the formula (XXXXVIIIg)
DE-A-3 721 786
h) compound of the formula (XXXXVIIIh)
EP-A-234 242
(48) compound of the formula (XXXXIX)
WO 96/23763
(49) compound of the formula (XXXXX)
EP-A-596 254
(50) compound of the formula (XXXXXI)
WO 98/23155
(50) compound of the formula (XXXXXII)
EP-A-569 384.

In addition to an active compound of the formula (I), the active compound combinations according to the invention comprise at least one active compound of the compounds of groups (1) to (51). Additionally, they may comprise further fungicidally active additives.

The synergistic effect is particularly pronounced when the active compounds in the active compound combinations according to the invention are present in certain weight ratios. However, the weight ratios of the active compounds in the active compound combinations can be varied within a relatively wide range. In general, from 0.1 to 50 parts by weight, preferably from 0.2 to 20 parts by weight, of active compound of group (1),
from 0.1 to 50 parts by weight, preferably from 0.2 to 20 parts by weight, of active compound of group (2),
from 1 to 150 parts by weight, preferably from 1 to 100 parts by weight, of active compound of group (3),
from 0.1 to 10 parts by weight, preferably from 0.2 to 5 parts by weight, of active compound of group (4),
from 1 to 150 parts by weight, preferably from 5 to 100 parts by weight, of active compound of group (5),
from 1 to 150 parts by weight, preferably from 5 to 100 parts by weight, of active compound of group (6),
from 0.1 to 50 parts by weight, preferably from 1 to 20 parts by weight, of active compound of group (7),
from 0.1 to 50 parts by weight, preferably from 0.2 to 20 parts by weight, of active compound of group (8),
from 0.02 to 50 parts by weight, preferably from 0.1 to 10 parts by weight, of active compound of group (9),
from 0.1 to 50 parts by weight, preferably from 0.2 to 20 parts by weight, of active compound of group (10),
from 0.1 to 50 parts by weight, preferably from 0.2 to 20 parts by weight, of active compound of group (11),
from 0.1 to 50 parts by weight, preferably from 0.2 to 20 parts by weight, of active compound of group (12),
from 0.1 to 50 parts by weight, preferably from 0.2 to 20 parts by weight, of active compound of group (13),
from 0.1 to 50 parts by weight, preferably from 0.2 to 20 parts by weight, of active compound of group (14),
from 0.2 to 50 parts by weight, preferably from 1 to 20 parts by weight, of active compound of group (15),
from 0.1 to 50 parts by weight, preferably from 0.2 to 20 parts by weight, of active compound of group (16),
from 0.1 to 50 parts by weight, preferably from 0.2 to 20 parts by weight, of active compound of group (17),
from 1 to 150 parts by weight, preferably from 5 to 100 parts by weight, of active compound of group (18),
from 0.1 to 150 parts by weight, preferably from 1 to 100 parts by weight, of active compound of group (19),
from 0.02 to 50 parts by weight, preferably from 0.2 to 10 parts by weight, of active compound of group (20),
from 0.05 to 20 parts by weight, preferably from 0.1 to 10 parts by weight, of active compound of group (21),
from 0.1 to 50 parts by weight, preferably from 0.2 to 20 parts by weight, of active compound of group (22),
from 0.1 to 50 parts by weight, preferably from 0.2 to 20 parts by weight, of active compound of group (23),
from 0.01 to 150 parts by weight, preferably from 1 to 100 parts by weight, of active compound of group (24),
from 0.1 to 50 parts by weight, preferably from 0.2 to 20 parts by weight, of active compound of group (25),
from 0.1 to 50 parts by weight, preferably from 0.2 to 20 parts by weight, of active compound of group (26),
from 0.1 to 50 parts by weight, preferably from 0.2 to 20 parts by weight, of active compound of group (27),
from 1 to 150 parts by weight, preferably from 5 to 100 parts by weight, of active compound of group (28), from 1 to 150 parts by weight, preferably from 5 to 100 parts by weight, of active compound of group (29), from 0.1 to 50 parts by weight, preferably from 0.2 to 20 parts by weight, of active compound of group (30), from 0.1 to 50 parts by weight, preferably from 0.2 to 20 parts by weight, of active compound of group (31), from 0.1 to 50 parts by weight, preferably from 0.2 to 20 parts by weight, of active compound of group (32), from 0.1 to 50 parts by weight, preferably from 0.2 to 20 parts by weight, of active compound of group (33), from 0.1 to 50 parts by weight, preferably 1 to 20 parts by weight, of active compound of group (34), from 0.1 to 50 parts by weight, preferably from 1 to 10 parts by weight, of active compound of group (35), from 1 to 150 parts by weight, preferably from 5 to 100 parts by weight, of active compound of group (36), from 0.1 to 50 parts by weight, preferably from 0.2 to 20 parts by weight, of active compound of group (37).

from 0.1 to 50 parts by weight, preferably from 0.2 to 20 parts by weight, of active compound of group (38), from 0.1 to 50 parts by weight, preferably from 0.2 to 20 parts by weight, of active compound of group (39), from 0.1 to 50 parts by weight, preferably from 0.2 to 20 parts by weight, of active compound of group (40), from 1 to 150 parts by weight, preferably from 5 to 100 parts by weight, of active compound of group (41), from 1 to 150 parts by weight, preferably from 5 to 100 parts by weight, of active compound of group (42), from 0.1 to 50 parts by weight, preferably from 1 to 20 parts by weight, of active compound of group (43), from 0.1 to 50 parts by weight, preferably from 1 to 20 parts by weight, of active compound of group (44), from 1 to 150 parts by weight, preferably from 5 to 100 parts by weight, of active compound of group (45a), from 1 to 150 parts by weight, preferably from 5 to 100 parts by weight, of active compound of group (45b), from 0.1 to 50 parts by weight, preferably from 0.2 to 20 parts by weight, of active compound of group (46), from 0.1 to 50 parts by weight, preferably from 0.2 to 20 parts by weight, of active compound of group (47a), from 0.1 to 50 parts by weight, preferably from 0.2 to 20 parts by weight, of active compound of group (47b), from 0.1 to 50 parts by weight, preferably from 0.2 to 20 parts by weight, of active compound of group (47c), from 0.1 to 50 parts by weight, preferably from 0.2 to 20 parts by weight, of active compound of group (47d), from 0.1 to 50 parts by weight, preferably from 0.2 to 20 parts by weight, of active compound of group (47e), from 0.1 to 50 parts by weight, preferably from 0.2 to 20 parts by weight, of active compound of group (47f), from 0.1 to 50 parts by weight, preferably 0.2 to 20 parts by weight, of active compound of group (47g), from 0.1 to 50 parts by weight, preferably from 0.2 to 20 parts by weight, of active compound of group (47h), from 0.1 to 50 parts by weight, preferably 0.2 to 20 parts by weight, of active compound of group (48), from 0.1 to 50 parts by weight, preferably from 0.2 to 20 parts by weight, of active compound of group (49), from 0.1 to 50 parts by weight, preferably from 0.2 to 20 parts by weight, of active compound of group (50), from 0.1 to 50 parts by weight, preferably from 0.2 to 20 parts by weight, of active compound of group (51)

are present per part by weight of active compound of the formula (I).

The active compound combinations according to the invention have very good fungicidal properties and can be employed for controlling phytopathogenic fungi, such as Plasmodiophoromycetes, Oomycetes, Chytridiomycetes, Zygomycetes, Ascomycetes, Basidiomycetes, Deuteromycetes, etc.

The active compound combinations according to the invention are particularly suitable for controlling *Phytophthora infestans* and *Plasmopara viticola*.

The fact that the active compound combinations are well tolerated by plants at the concentrations required for controlling plant diseases permits the treatment of above-ground parts of plants, of propagation stock and seeds, and of the soil. The active compound combinations according to the invention can be employed for foliar application or else as seed dressings.

The active compound combinations according to the invention may also be employed to increase the yield of crops. However, they have reduced toxicity and are tolerated well by plants.

According to the invention, it is possible to treat all plants and parts of plants. Plants are to be understood here as meaning all plants and plant populations such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including plant cultivars which can or cannot be protected by plant breeders certificates. Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. Parts of plants also include harvested plants and vegetative and generative propagation material, for example seedlings, tubers, rhizomes, cuttings and seeds.

The treatment of the plants and parts of plants according to the invention with the active compounds is carried out directly or by action on their environment, habitat or storage area according to customary treatment methods, for example by dipping, spraying, evaporating, atomizing, broadcasting, brushing-on and, in the case of propagation material, in particular in the case of seeds, furthermore by one- or multi-layer coating.

The active compound combinations according to the invention can be converted to the customary formulations, such as solutions, emulsions, suspensions, powders, foams, pastes, granules, aerosols and microencapsulations in polymeric substances and in coating compositions for seeds, and ULV formulations.

These formulations are produced in a known manner, for example by mixing the active compounds or active compound combinations with extenders, that is liquid solvents, liquefied gases under pressure, and/or solid carriers, optionally with the use of surfactants, that is emulsifiers and/or dispersants, and/or foam formers. If the extender used is water, it is also possible to use, for example, organic solvents as auxiliary solvents. Essentially, suitable liquid solvents include: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water. Liquefied gaseous extenders or carriers are to be understood as meaning liquids which are gaseous at ambient temperature and under atmospheric pressure, for example aerosol propellants such as butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as finely divided silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are: for example ligninsulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other additives can be mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95% by weight of active compounds, preferably between 0.5 and 90%.

The active compound combinations according to the invention, as such or in their formulations, can also be applied in a mixture with known fungicides, bactericides, acaricides, nematicides or insecticides, to broaden the activity spectrum or to prevent the development of resistance, for example. In many cases, synergistic effects are obtained, i.e. the activity of the mixture is greater than the activity of the individual components.

A mixture with other known active compounds such as herbicides or with fertilizers and growth regulators is also possible.

The active compound combinations can be used as such, in the form of their formulations or as the use forms prepared therefrom, such as ready-to-use solutions, emulsifiable concentrates, emulsions, suspensions, wettable powders, soluble powders and granules. They are used in the customary manner, for example by watering, spraying, atomizing, scattering, spreading, and as a powder for dry seed treatment, a solution for seed treatment, a water-soluble powder for seed treatment, a water-soluble powder for slurry treatment, or by encrusting.

When using the active compound combinations according to the invention, the application rates can be varied within a relatively wide range, depending on the kind of application. In the treatment of parts of plants, the application rates of the active compound combination are generally between 0.1 and 10,000 g/ha, preferably between 10 and 1000 g/ha. In the treatment of seeds, the application rates of the active compound combination are generally between 0.001 and 50 g per kilogram of seed, preferably between 0.01 and 10 g per kilogram of seed. In the treatment of the soil, the application rates of the active compound combination are generally between 0.1 and 10,000 g/ha, preferably between 1 and 5000 g/ha.

The good fungicidal activity of the active compound combinations according to the invention is evident from the examples below. While the individual active compounds exhibit weaknesses with regard to the fungicidal activity, the combinations have an activity which exceeds the sum of individual activities.

A synergistic effect of fungicides is always present when the fungicidal activity of the active compound combinations exceeds the total of the activities of the active compounds when applied individually.

The expected activity for a given combination of two active compounds can be calculated as follows (cf. Colby, S. R., "Calculating Synergistic and Antagonistic Responses of Herbicide Combinations", Weeds 15, (1967), 20-22):

If

X is the efficacy when applying active compound A at an application rate of m g/ha, Y is the efficacy when applying active compound B at an application rate of n g/ha and E is the efficacy when applying the active compounds A and B at an application rate of m and n g/ha, then $$E = X + Y - \frac{X \cdot Y}{100}$$

The efficacy is calculated in %. 0% is an efficacy which corresponds to that of the control, whereas an efficacy of 100% means that no infection is observed.

If the actual fungicidal activity exceeds the calculated value, then the activity of the combination is superadditive, i.e. a synergistic effect exists. In this case, the efficacy which was actually observed must be greater than the value for the expected efficacy (E) calculated from the abovementioned formula.

The examples that follow illustrate the invention. However, the invention is not limited to the examples.

EXAMPLE 1

*Phytophthora* Test (Tomato)/Protective

| Solvent: | 47 parts by weight of acetone |
| Emulsifier: | 3 parts by weight of alkylaryl polyglycol ether |

To produce a suitable preparation of active compound, 1 part by weight of active compound or active compound combination is mixed with the stated amounts of solvent and emulsifier, and the concentrate is diluted with water to the desired concentration, or a commercial formulation of active compound or active compound combination is diluted with water to the desired concentration.

To test for protective activity, young plants are sprayed with the active compound preparation at the stated application rate. After the spray coating has dried on, the plants are inoculated with an aqueous spore suspension of *Phytophthora infestans*. The plants are then placed in an incubation cabin at about 20° C. and 100% relative atmospheric humidity.

Evaluation is carried out 3 days after the inoculation. 0% means an efficacy which corresponds to that of the control, whereas an efficacy of 100% means that no infection is observed.

The activity found for the active compound combination according to the invention is greater than the calculated activity, i.e. there is a synergistic effect. At a mixing ratio of 1:1 and an application rate of 0.1 g/ha, the combination of the compound of the formula (1) and the halogeno-benzimidazole of the formula No. XXVII has an actual efficacy of 73%. At 63%, the expected value, calculated using Colby's formula, is considerably lower.

Active compounds, application rates and test results are shown in the tables below.

TABLE 1

Phytophthora test (tomato)/protective

| Active compound known: | Active compound application rate in g/ha | Efficacy in % |
|---|---|---|
| compound of the formula (XXVII) | 0.1 | 30 |
| compound of the formula (I) | 0.1 | 47 |

Mixture according to the invention:

| Active compound | Mixing ratio | Active compound application rate in g/ha | Actual efficacy | Expected value, calculated using Colby's formula |
|---|---|---|---|---|
| XXVII + I | 1:1 | 0.1 + 0.1 | 73 | 63 |

TABLE 2

Phytophthora test (tomato)/protective

| Active compound known: | Active compound application rate in g/ha | Efficacy in % |
|---|---|---|
| compound of the formula (I) | 1 | 47 |
| propineb (VI) | 20 | 19 |

$-[Zn-S-\overset{S}{\underset{\|}{C}}-NH-CH_2-\overset{CH_3}{\underset{|}{CH}}-NH-\overset{S}{\underset{\|}{C}}-S]_n-$
n >= 1 (propineb) (VI)

Mixture according to the invention

| Active compound | Mixing ratio | Active compound application rate in g/ha | Actual efficacy | Expected value calculated using Colby's formula |
|---|---|---|---|---|
| (I) + propineb (VI) | 1:20 | 1 + 20 | 94 | 57 |

TABLE 3

Phytophthora test (tomato)/protective

| Active compound known: | Active compound application rate in g/ha | Efficacy in % |
|---|---|---|
| compound of the formula (I) | 1 | 47 |
| chlorothalonil (XXIX) | 20 | 12 |

Mixture according to the invention

| Mixing ratio | Active compound application rate in g/ha | Actual efficacy | Expected value calculated using Colby's formula |
|---|---|---|---|
| (I) + chlorothalonil (XXIX) | 1:20 | 1 + 20 | 84 | 53 |

TABLE 4

Phytophthora test (tomato)/protective

| Active compound known: | Active compound application rate in g/ha | Efficacy in % |
|---|---|---|
| compound of the formula (I) | 1 | 47 |
| dichlofluanid (IVa) | 20 | 5 |

Mixture according to the invention:

| Mixing ratio | Active compound application rate in g/ha | Actual efficacy | Expected value calculated using Colby's formula |
|---|---|---|---|
| (I) + dichlofluanid (IVa) | 1:20 | 1 + 20 | 87 | 50 |

TABLE 5

Phytophthora test (tomato)/protective

| Active compound known: | Active compound application rate in g/ha | Efficacy in % |
|---|---|---|
| compound of the formula (I) | 1 | 47 |
| tolylfluanid (IVb) | 20 | 21 |

Mixture according to the invention:

| | Mixing ratio | Active compound application rate in g/ha | Actual efficacy | Expected value calculated using Colby's formula |
|---|---|---|---|---|
| (I) + tolylfluanid (IVa) | 1:20 | 1 + 20 | 95 | 58 |

TABLE 6

Phytophthora test (tomato)/protective

| Active compound known: | Active compound application rate in g/ha | Efficacy in % |
|---|---|---|
| compound of the formula (I) | 1 | 47 |
| folpet (XIX) | 20 | 0 |

Mixture according to the invention:

| | Mixing ratio | Active compound application rate in g/ha | Actual efficacy | Expected value calculated using Colby's formula |
|---|---|---|---|---|
| (I) + folpet (XIX) | 1:20 | 1 + 20 | 95 | 47 |

TABLE 7

Phytophthora test tomato/protective

| Active compound known: | Active compound application rate in g/ha | Efficacy in % |
|---|---|---|
| compound of the formula (I) | 1 | 39 |
| mancozeb (VIIc) | 20 | 28 |

Mixture according to the invention:

| | Mixing ratio | Active compound application rate in g/ha | Actual efficacy | Expected value calculated using Colby's formula |
|---|---|---|---|---|
| (I) + mancozeb (VIIc) | 1:20 | 1 + 20 | 68 | 56 |

TABLE 8

Phytophthora test (tomato)/protective

| Active compound known: | Active compound application rate in g/ha | Efficacy in % |
|---|---|---|
| compound of the formula (I) | 1 | 47 |
| bitertanol (IIc) | 10 | 4 |

Mixture according to the invention:

| | Mixing ratio | Active compound application rate in g/ha | Actual efficacy | Expected value calculated using Colby's formula |
|---|---|---|---|---|
| (I) + bitertanol (IIc) | 1:10 | 1 + 10 | 73 | 49 |

TABLE 9

Phytophthora test (tomato)/protective

| Active compound known: | Active compound application rate in g/ha | Efficacy in % |
|---|---|---|
| compound of the formula (I) | 1 | 47 |

TABLE 9-continued

Phytophthora test (tomato)/protective

| | | |
|---|---|---|
| tebuconazole (III) | 10 | 5 |

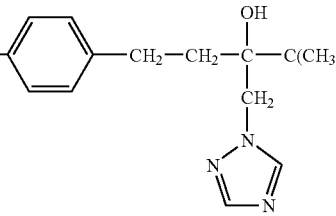

Mixture according to the invention:

| Mixing ratio | Active compound application rate in g/ha | Actual efficacy | Expected value calculated using Colby's formula |
|---|---|---|---|
| (I) + tebuconazole (III)   1:10 | 1 + 10 | 73 | 50 |

TABLE 10

Phytophthora test (tomato)/protective

| Active compound known: | Active compound application rate in g/ha | Efficacy in % |
|---|---|---|
| compound of the formula (I) | 1 | 47 |

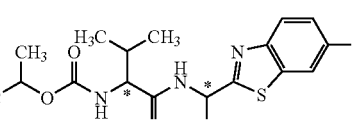

| triadimenol (IIb) | 10 | 0 |
|---|---|---|

Mixture according to the invention:

| Mixing ratio | Active compound application rate in g/ha | Actual efficacy | Expected value calculated using Colby's formula |
|---|---|---|---|
| (I) + triadimenol (IIb)   1:10 | 1 + 10 | 88 | 47 |

TABLE 11

Phytophthora test (tomato)/protective

| Active compound known: | Active compound application rate in g/ha | Efficacy in % |
|---|---|---|
| compound of the formula (I) | 1 | 47 |

TABLE 11-continued

Phytophthora test (tomato)/protective

| | | |
|---|---|---|
| imidacloprid (XXII) | 10 | 0 |

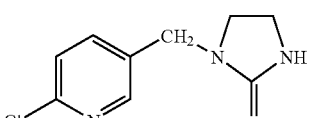

Mixture according to the invention:

| Mixing ratio | Active compound application rate in g/ha | Actual efficacy | Expected value calculated using Colby's formula |
|---|---|---|---|
| (I) + imidacloprid (XXII)   1:10 | 1 + 10 | 71 | 47 |

TABLE 12

Phytophthora test (tomato)/protective

| Active compound known: | Active compound application rate in g/ha | Efficacy in % |
|---|---|---|
| compound of the formula (I) | 1 | 47 |
| compound of the formula (XXI) (20) | 10 | 2 |

(XXI)

Mixture according to the invention:

| Mixing ratio | Active compound application rate in g/ha | Actual efficacy | Expected value calculated using Colby's formula |
|---|---|---|---|
| (I) + (XXI) (20)   1:10 | 1 + 10 | 62 | 48 |

TABLE 13

Phytophthora test (tomato)/protective

| Active compound known: | Active compound application rate in g/ha | Efficacy in % |
|---|---|---|
| compound of the formula (I) | 1 | 47 |
| fenhexamid (VIII) | 10 | 13 |

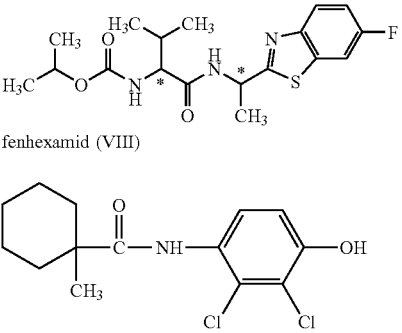

Mixture according to the invention:

| | Mixing ratio | Active compound application rate in g/ha | Actual efficacy | Expected value calculated using Colby's formula |
|---|---|---|---|---|
| (I) + fenhexamid (VIII) | 1:10 | 1 + 10 | 70 | 54 |

TABLE 14

Phytophthora test (tomato)/protective

| Active compound known: | Active compound application rate in g/ha | Efficacy in % |
|---|---|---|
| compound of the formula (I) | 1 | 47 |
| carpropamid (V) | 10 | 0 |

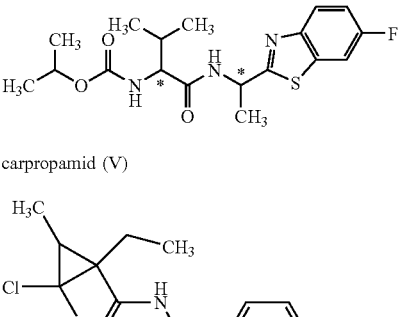

Mixture according to the invention:

| | Mixing ratio | Active compound application rate in g/ha | Actual efficacy | Expected value calculated using Colby's formula |
|---|---|---|---|---|
| (I) + carpropamid (V) | 1:10 | 1 + 10 | 90 | 47 |

TABLE 15

Phytophthora test (tomato)/protective

| Active compound known: | Active compound application rate in g/ha | Efficacy in % |
|---|---|---|
| compound of the formula (I) | 1 | 47 |
| spiroxamine (XI) | 10 | 0 |

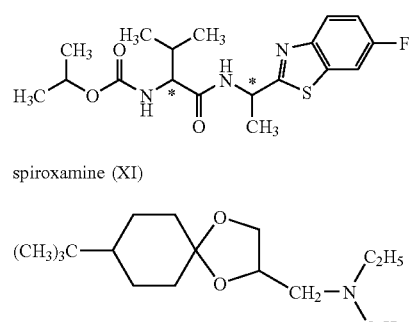

Mixture according to the invention:

| | Mixing ratio | Active compound application rate in g/ha | Actual efficacy | Expected value calculated using Colby's formula |
|---|---|---|---|---|
| (I) + spiroxamine (XI) | 1:10 | 1 + 10 | 86 | 47 |

TABLE 16

Phytophthora test (tomato)/protective

| Active compound known: | Active compound application rate in g/ha | Efficacy in % |
|---|---|---|
| compound of the formula (I) | 1 | 39 |
| fluazinam (XXXI) | 10 | 56 |

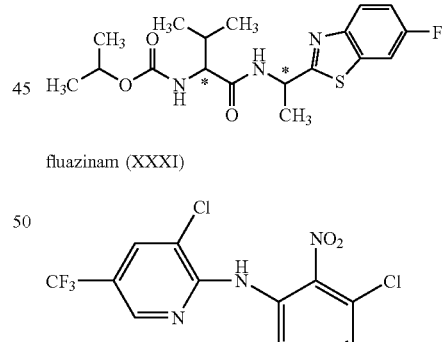

Mixture according to the invention:

| | Mixing ratio | Active compound application rate in g/ha | Actual efficacy | Expected value calculated using Colby's formula |
|---|---|---|---|---|
| (I) + fluazinam (XXXI) | 1:10 | 1 + 10 | 87 | 73 |

TABLE 17

Phytophthora test (tomato)/protective

| Active compound known: | Active compound application rate in g/ha | Efficacy in % |
|---|---|---|
| compound of the formula (I) | 1 | 47 |
| compound of the formula (XXVIII)(27) | 1 | 9 |

Mixture according to the invention:

| Mixing ratio | Active compound application rate in g/ha | Actual efficacy | Expected value calculated using Colby's formula |
|---|---|---|---|
| (I) + (XXVIII) (27) | 1:1 | 1 + 1 | 72 | 52 |

TABLE 18

Phytophthora test (tomato)/protective

| Active compound known: | Active compound application rate in g/ha | Efficacy in % |
|---|---|---|
| compound of the formula (I) | 1 | 47 |
| compound of the formula (XIV) (13) | 1 | 8 |

Mixture according to the invention:

| Mixing ratio | Active compound application rate in g/ha | Actual efficacy | Expected value calculated using Colby's formula |
|---|---|---|---|
| (I) + (XIV) (13) | 1:1 | 1 + 1 | 62 | 51 |

TABLE 19

Phytophthora test (tomato)/protective

| Active compound known: | Active compound application rate in g/ha | Efficacy in % |
|---|---|---|
| formula (I) | 1 | 56 |
| compound of the formula (XXXXVIa) (40) copper oxychloride | 50 | 0 |

Mixture according to the invention:

| Mixing ratio | Active compound application rate in g/ha | Actual efficacy | Expected value calculated using Colby's formula |
|---|---|---|---|
| formula (I) + copper oxychloride (XXXXVIa) | 1:50 | 1 + 50 | 82 | 56 |

TABLE 20

Phytophthora test (tomato)/protective

| Active compound known: | Active compound application rate in g/ha | Efficacy in % |
|---|---|---|
| formula (I) | 1 | 56 |
| compound of the formula (XII) (11) azoxystrobin | 1 | 55 |

TABLE 20-continued

Phytophthora test (tomato)/protective
Mixture according to the invention:

| Mixing ratio | Active compound application rate in g/ha | Actual efficacy | Expected value calculated using Colby's formula |
|---|---|---|---|
| formula (I) + azoxystrobin (XII) (XXII) 1:1 | 1 + 1 | 95 | 80 |

TABLE 21

Phytophthora test (tomato)/protective

| Active compound known: | Active compound application rate in g/ha | Efficacy in % |
|---|---|---|
| formula (I) | 1 | 56 |

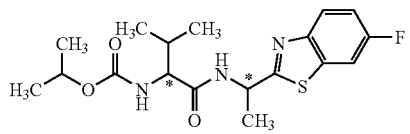

| compound of the formula (XIII) (12) trifloxystrobin | 1 | 0 |

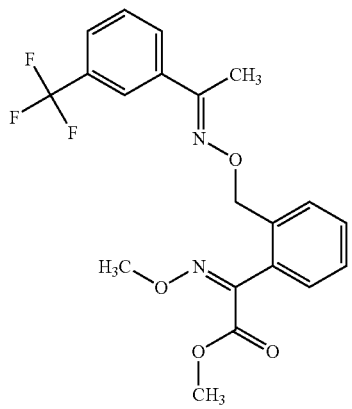

TABLE 21-continued

Phytophthora test (tomato)/protective
Mixture according to the invention:

| Mixing ratio | Active compound application rate in g/ha | Actual efficacy | Expected value calculated using Colby's formula |
|---|---|---|---|
| formel (I) + trifloxystrobin (XXIII) 1:1 | 1 + 1 | 68 | 56 |

The invention claimed is:

1. An active compound combination comprising at least one compound of formula (I)

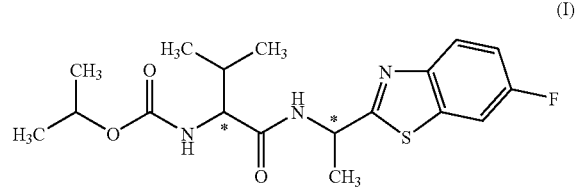

and the tetrachloro-isophthalo-dinitrile of formula (XXIX)

(XXIX)

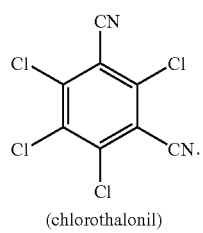

(chlorothalonil)

2. An active compound combination according to claim 1 wherein the weight ratio of the compound of the formula (I) to the compound of the formula (XXIX) is from 1:1 to 1:150.

* * * * *